United States Patent
Fällman (10) Patent No.: US 8,267,959 B2
(45) Date of Patent: Sep. 18, 2012

(54) TECHNIQUE FOR SECURING A SUTURE

(75) Inventor: David Fällman, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 550 days.

(21) Appl. No.: 10/805,486

(22) Filed: Mar. 22, 2004

(65) Prior Publication Data
US 2005/0137624 A1 Jun. 23, 2005

Related U.S. Application Data (60) Provisional application No. 60/530,618, filed on Dec. 19, 2003.

(51) Int. Cl.
*A61B 17/08* (2006.01)
(52) U.S. Cl. ........................................ 606/215; 606/232
(58) Field of Classification Search .......... 606/228–232, 606/72, 213, 215, 216, 151; 57/22, 201; 24/38
See application file for complete search history.

(56) References Cited

U.S. PATENT DOCUMENTS

| | | | |
|---|---|---|---|
| 330,087 A * | 11/1885 | Binns | 474/253 |
| 5,062,344 A | 11/1991 | Gerker | |
| 5,540,703 A | 7/1996 | Barker, Jr. et al. | |
| 5,620,461 A * | 4/1997 | Muijs Van De Moer et al. | 606/213 |
| 5,683,417 A | 11/1997 | Cooper | |
| 5,699,657 A * | 12/1997 | Paulson | 57/22 |
| 6,296,659 B1 | 10/2001 | Foerster | |
| 6,425,911 B1 | 7/2002 | Akerfeldt et al. | |
| 6,503,267 B2 * | 1/2003 | Bonutti et al. | 606/232 |
| 6,508,828 B1 | 1/2003 | Akerfeldt et al. | |
| 6,746,472 B2 * | 6/2004 | Frazier et al. | 606/232 |
| 6,929,655 B2 | 8/2005 | Egnelöv et al. | |
| 7,025,756 B2 * | 4/2006 | Frazier et al. | 604/500 |
| 7,153,312 B1 * | 12/2006 | Torrie et al. | 606/144 |
| 2002/0029066 A1 | 3/2002 | Foerster | |
| 2002/0161168 A1 * | 10/2002 | Shalaby et al. | 528/310 |
| 2003/0149448 A1 * | 8/2003 | Foerster et al. | 606/232 |
| 2004/0093025 A1 * | 5/2004 | Egnelov | 606/214 |
| 2004/0138589 A1 | 7/2004 | Egnelov et al. | |
| 2004/0138674 A1 | 7/2004 | Egnelov et al. | |
| 2004/0254593 A1 * | 12/2004 | Fallin et al. | 606/148 |

* cited by examiner

*Primary Examiner* — Katherine Dowe
(74) *Attorney, Agent, or Firm* — Foley & Lardner LLP (57) ABSTRACT

A device to seal an incision in a blood vessel includes an inner member and an outer member. A suture connects the inner member and the outer member. A first portion of the suture is embedded within a second portion of the suture such that as tension in the suture increases the first and second portions are held together.

19 Claims, 6 Drawing Sheets

TECHNIQUE FOR SECURING A SUTURE

CROSS-REFERENCE TO RELATED PATENT APPLICATIONS

The Applicant claims the benefit of U.S. Provisional Application No. 60/530,618, filed Dec. 19, 2003, whose entire contents are incorporated herein by reference.

BACKGROUND OF THE INVENTION

There are several medical procedures which require access to a patient's vascular system. Access to a patient's vascular system can be provided by making an incision (sometimes called a puncture, wound, or hole) in an artery (or other blood vessel) below the skin surface. At the conclusion of the medical procedure, the incision in the artery must be sealed.

One technique for sealing such an incision is to place an inner seal within the artery and an outer locking element outside the artery in such a fashion as to seal the incision. The seal is made of bioabsorbable materials which are absorbed within the body over time. The inner seal, the outer locking element, and the suture are usually components of an introducer and sealing assembly. A suture loop is needed to guide and hold the seal, the locking element, and the suture during the sealing procedure. The suture (for example, a thread or a multifilament fiber) holds the inner seal in place and guides the locking element to a position outside of the artery opposite the inner seal. Typically, in such a suture loop, the ends (or other portions) of the suture are glued or tied together to complete the loop.

Similar suture loops can also be used when a closure comprises an inner anchor member and an outer seal, e.g., in the form of a collagen plug, which are held together by a suture loop, or when an outer member and an inner member are clamped together to thereby seal a puncture in an intermediate blood vessel wall.

Additional background on the techniques described above is set forth in U.S. Pat. Nos. 6,508,828 and 6,425,911, and U.S. patent application Ser. Nos. 10/280,086, 10/341,599, and 10/341,598, whose entire contents are incorporated herein by reference.

SUMMARY OF THE INVENTION

It has been discovered that the use of glue or knot(s) to form the loop has disadvantages. For example, the use of glue in the manufacturing process complicates manufacturing because the glue has to be applied properly, has to be immobilized while drying, etc. Knot(s) reduce the strength of a suture, and make the overall design more complicated because care must be taken to make sure that the knot(s) pass through various components (e.g., components of an introducer device used to guide and push the sealing and/or locking members in place during a sealing procedure).

The present invention provides a technique to connect the ends (or other portions) of a suture used in sealing an incision in a blood vessel. In the present invention, portions of the suture are joined together (for example, to form a loop) by embedding one portion of the suture within another portion of the suture, such that as tension in the suture increases, the different portions of the suture are held together. This joining may be accomplished using a needle, by sticking a suture into itself, by a splice, by weaving, by embedding, or by any other technique wherein tension in the suture maintains or increases the holding power.

The tension in the suture contracts (i.e., reduces the cross-sectional area of) the suture such that the friction force between the walls of the suture portions (i.e., between a first portion and a second portion, which is enclosed by the first portion) increases and becomes larger than the force (tension) that tries to separate the portions (i.e., larger than the force pulling the two portions apart).

BRIEF DESCRIPTION OF THE DRAWINGS

Preferred embodiments of the invention are shown in the drawings wherein:

FIGS. 7(a) to 11 illustrate sixth to tenth embodiments of the invention.

DETAILED DESCRIPTION OF THE PREFERRED EMBODIMENTS

Figure 1:
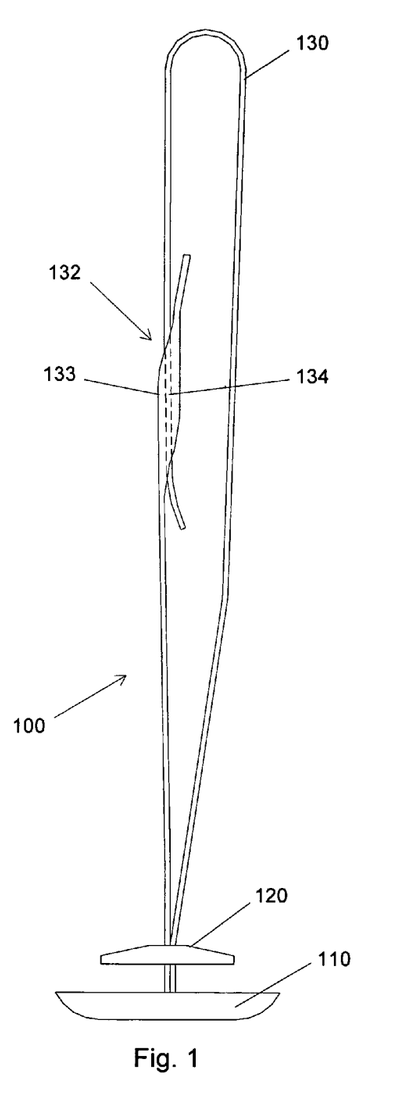
FIG. 1 illustrates one embodiment of the invention wherein a suture is embedded in itself.

FIG. 1 illustrates a first preferred embodiment 100. As shown in FIG. 1, first preferred embodiment 100 includes an inner seal 110, an outer locking element 120, and a suture 130. The suture 130 has a portion 132 wherein a first portion 134 of the suture is embedded in a second portion 133 of the suture, as shown in FIG. 1. In this manner, as tension in the suture increases, the portions 133 and 134 are held together due to portion 133 contracting (in cross section) and exerting friction on portion 134.

Figure 2A:
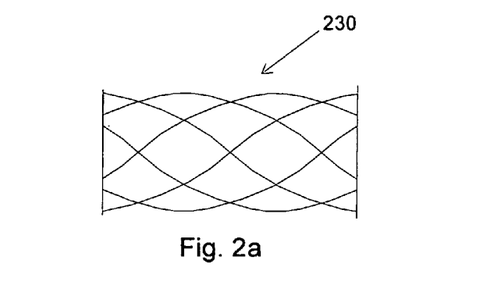
FIGS. 2a to 2d illustrate various sutures suitable for use in the invention.
Figure 2B:
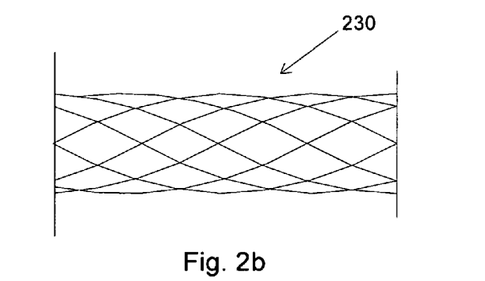
Figure 2C:
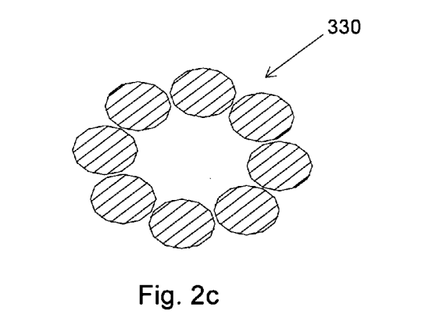
Figure 2D:
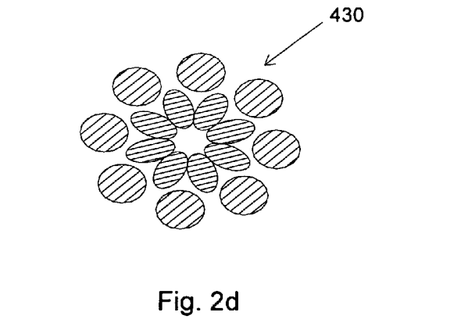

FIGS. 2a to 2d illustrate some examples of sutures which may be employed in the present invention. FIG. 2a shows a suture 230 in a relaxed state and FIG. 2b shows the same suture 230 in a state of tension. FIG. 2c illustrates a suture 330 having a single layer of filaments and FIG. 2d shows a suture 430 having two layers of filaments. Other suture designs may be used in the invention.

Figure 3:
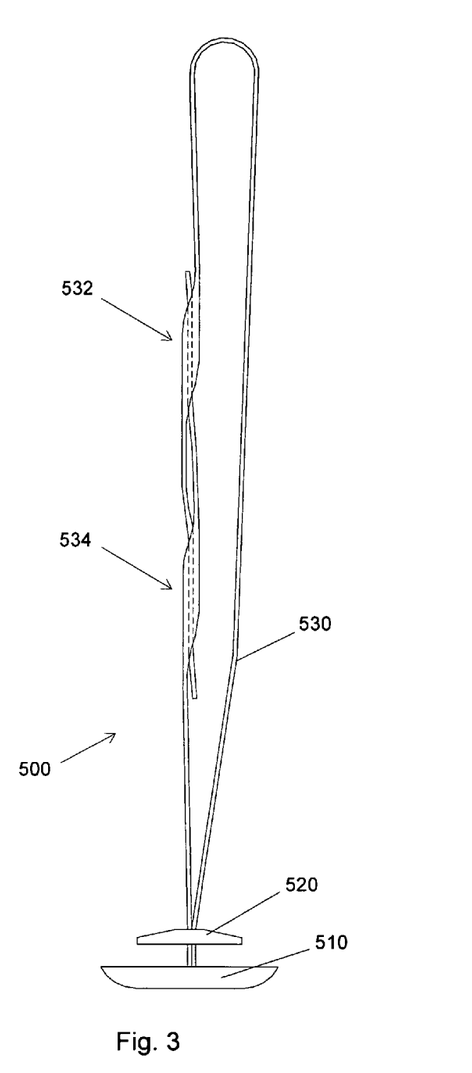
FIGS. 3 and 4 illustrate second and third embodiments of the invention wherein the suture is embedded in itself at multiple places for additional strength.

FIG. 3 illustrates a second embodiment 500. The second embodiment includes an inner seal 510 and a locking element 520. A suture 530 is used to connect inner seal 510 and locking element 520. In the second embodiment, there are two portions 532 and 534 wherein one portion of the suture is embedded within another portion of the suture such that as tension in the suture increases, the portions are held together. The second embodiment has the advantage over the first embodiment of additional strength.

Figure 4:
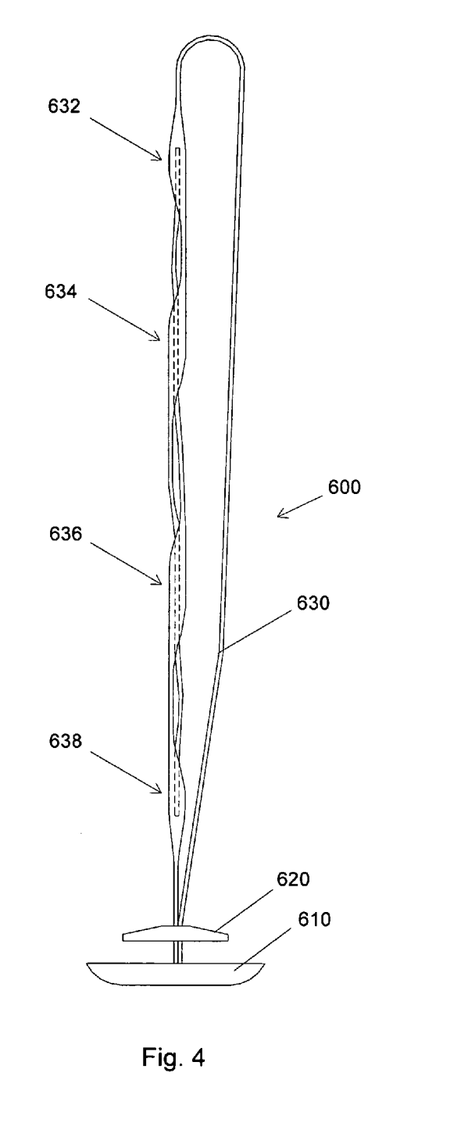

FIG. 4 illustrates a third embodiment 600 which includes an inner seal 610, a locking element 620, and a suture 630. The third embodiment 600 includes four portions 632, 634, 636, and 638 wherein one portion of the suture is embedded within another portion of the suture. In FIG. 4, the end portions of the suture have been embedded into the suture such that there are no portions that stick out and thus no portions that can get stuck during a sealing procedure.

Figure 5:
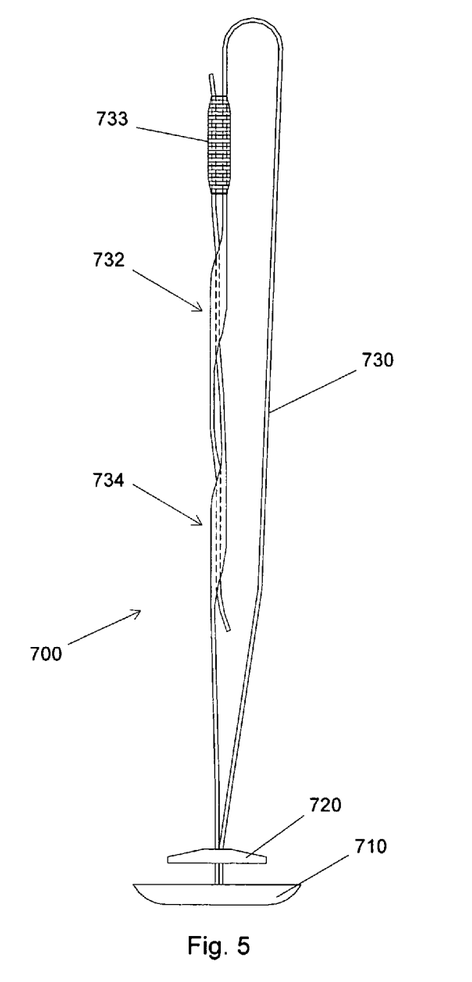
FIGS. 5 and 6 illustrate fourth and fifth embodiments which are similar to FIGS. 3 and 4 except that glue is also used to join the sutures in FIGS. 5 and 6.

FIG. 5 illustrates a fourth embodiment which includes an inner seal 710, a locking element 720, and a suture 730. In this fourth embodiment 700, two portions 732 and 734 are provided wherein a part of the suture is embedded within another part of the suture. The embodiment 700 also includes glue 733 which is used to fashion two portions of the suture together for added strength.

Figure 6:
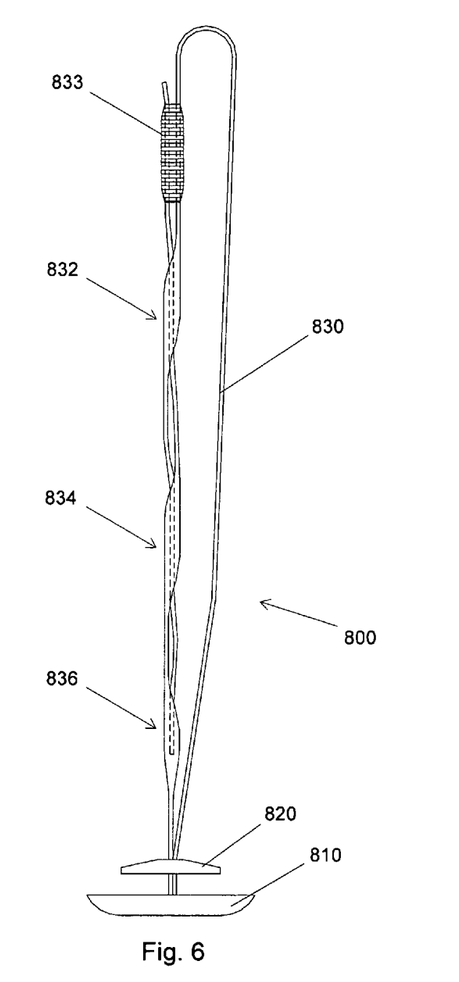

FIG. 6 illustrates a fifth embodiment 800 which includes an inner seal 810, a locking element 820, and a suture 830. Three portions 832, 834, and 836 are provided wherein one portion of the suture is embedded within another portion of the suture. The embodiment 800 also utilizes glue 833, similar to the fourth embodiment. In FIG. 6, one end portion of the suture is embedded into the suture and the other end portion is secured by glue at or near the end such that there are no portions that stick out and no portions that can get stuck.

Figures 7A, 7B:
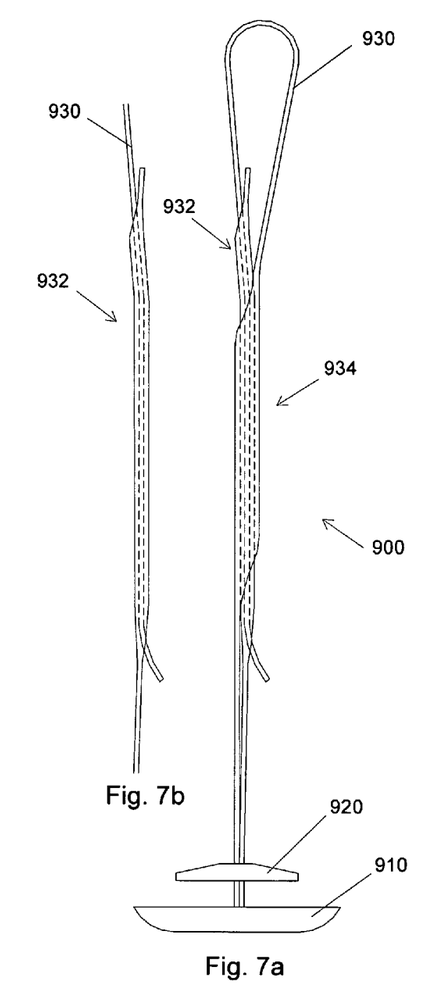

FIGS. 7*a* and 7*b* illustrate a sixth embodiment 900 which includes an inner seal 910, a locking element 920, and a suture 930. As shown in FIG. 7*b* (which illustrates a part of the arrangement of FIG. 7*a*, with other parts removed for clarity), the sixth embodiment 900 includes a portion 932 wherein one portion of the suture is embedded in another portion of the suture. As illustrated in FIG. 7*a*, this portion 932 is itself embedded within an additional portion 934.

Figures 8A, 8B:
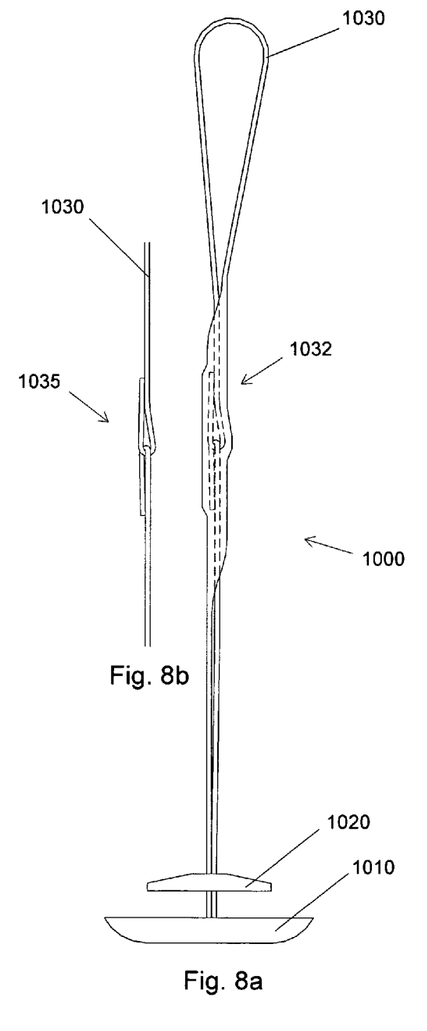

FIGS. 8*a* and 8*b* illustrate a seventh embodiment 1000, which includes an inner seal 1010, a locking element 1020, and a suture 1030. As shown in FIG. 8*b* (which illustrates a part of the arrangement illustrated in FIG. 8*a*, with other parts removed for clarity), the ends of the suture are looped around one another in an arrangement 1035. The arrangement 1035 is in turn embedded within a portion 1032 of the suture 1030.

Figure 9:
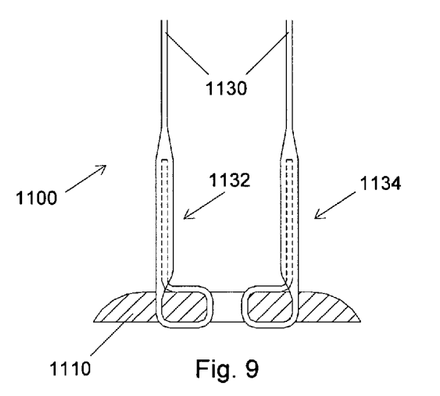
Figure 10:
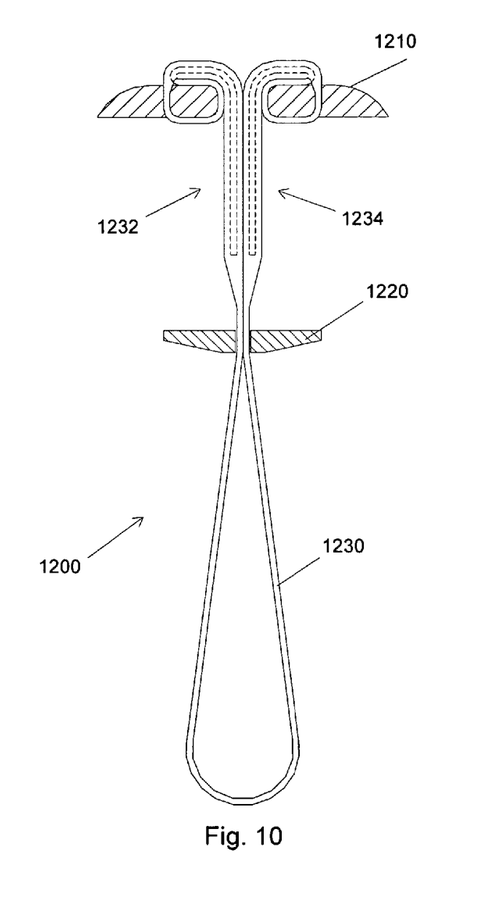

FIG. 9 illustrates an eighth embodiment 1100 which is used to connect an inner seal 1110 to a suture 1130. In the eighth embodiment 1100, the ends of the suture are looped around seal 1110 and then embedded into the suture at portions 1132 and 1134. FIG. 10 illustrates a ninth embodiment 1200, which includes an inner seal 1210, an outer locking element 1220, and a suture 1230. In this embodiment, the ends of suture 1230 are embedded into portions of the suture 1232 and 1234. In FIGS. 9 and 10, an enlarged cross-section created by the present way of joining portions of the suture is utilized to hold the inner seal and/or locking element in place by friction. In other words, the enlarged portions 1132, 1134, 1232, and 1234 can retain the locking element (e.g., locking element 1220) in place when the locking element is slid over these portions. A portion of the loop which has an enlarged thickness could be used to hold an outer member (or other member) in place by friction in the other embodiments. For example, the FIG. 7 embodiment could be modified to hold the outer member by placing the enlarged portion close to the inner member and adjusting the resilience and diameter of the hole in the outer member accordingly.

Figure 11:
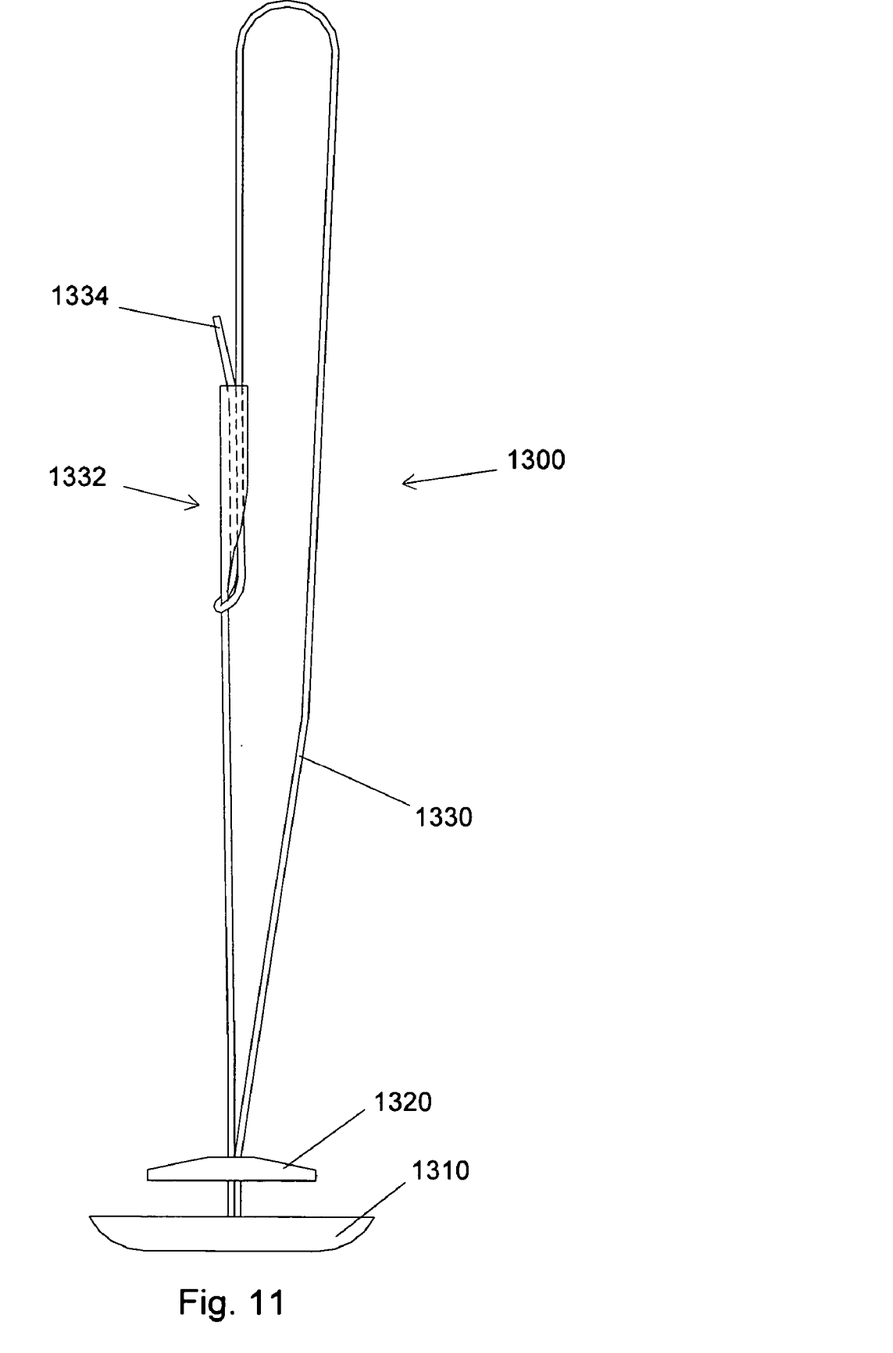

FIG. 11 illustrates a tenth embodiment 1300, which includes an inner seal 1310, a locking element 1320, and a suture 1330. In this embodiment, one end 1334 of suture 1330 is wrapped around the suture and then embedded in another portion of the suture, as shown in FIG. 11.

The foregoing description of preferred embodiments of the invention has been presented for purposes of illustration. It is not intended to be exhaustive or to limit the invention to the precise form disclosed, and modifications and variations are possible in light of the above teachings. It is intended that the scope of the invention be defined with reference to the claims appended hereto, and their equivalents.

What is claimed is:

1. A device to seal an incision in a blood vessel, comprising:
an inner member;
an outer member; and
a suture connected to the inner member and the outer member, wherein a first portion of the suture is embedded within a second portion of the suture at an embedded portion such that as tension in the suture increases the first and second portions are held together,
wherein the second portion completely encircles the first portion at at least one cross section, and
wherein at least one of the inner member and the outer member are configured to seal an incision in a blood vessel,
wherein the suture, the inner member and the outer member are arranged such that the inner member and the outer member lie opposite to one another with at least a portion of the suture in-between the inner member and the outer member, with the outer member being moveable along said portion towards the inner member,
wherein the entire portion of the suture extending from the inner member to the outer member has no knots,
wherein the device to seal an incision in a blood vessel further comprises an introducer device, adapted to guide and push the inner member and the outer member in place during a sealing procedure, wherein the suture passes through the introducer device,
wherein the suture has a first end at one bitter end of the suture and a second end at another bitter end of the suture and the suture is configured such that the first and second ends pass by each other in opposite directions such that the first end and the second end are on opposite sides of the embedded portion,
wherein the suture forms a loop of fixed, unvariable length,
wherein all ends of the suture are buried within the suture such that no suture ends are visible at any time,
wherein the suture bitter ends are made of suture material.

2. A device as set forth in claim 1, wherein the inner member comprises a seal configured to seal the incision in the blood vessel by contacting an inner surface wall of the blood vessel around the entire circumference of the incision.

3. A device as set forth in claim 1, wherein the outer member comprises a seal configured to seal the incision in the blood vessel by contacting an outer surface wall of the blood vessel around the entire circumference of the incision.

4. A device as set forth in claim 1, wherein the outer member comprises a collagen plug.

5. A device as set forth in claim 1, wherein a third portion of the suture is embedded within a fourth portion of the suture such that as tension in the suture increases the third and fourth portions are held together.

6. A device as set forth in claim 5, further comprising glue to secure different portions of the suture together.

7. A device as set forth in claim 5, wherein the second portion and the fourth portion are configured to retain the outer member in place when the outer member is slid over the second portion and the fourth portion.

8. A device as set forth in claim 1, wherein the first portion comprises at least one suture loop.

9. A device as set forth in claim 1, wherein the first portion comprises at least two suture loops.

10. A device as set forth in claim 1, further comprising a third portion around the second portion such that as tension in the suture increases the second and third portions are held together.

11. A device as set forth in claim 1, wherein the suture further comprises a third portion of the suture embedded within the second portion of the suture such that as tension in the suture increases the first, second, and third portions are held together.

12. A device as set forth in claim 1, wherein the inner member comprises an anchor.

13. A device as set forth in claim 1, wherein the outer member comprises a locking element.

14. A device as set forth in claim 1, wherein the first portion and the second portion are configured to help retain the outer member in place when the outer member is slid over the first portion and the second portion.

15. The device as set forth in claim 1, wherein as tension in the suture increases the first portion and the second portion are held together due to at least one of the first portion and the second portion contracting in cross section and exerting force on at least one of the second portion and the first portion.

16. A device to seal an incision in a blood vessel, comprising:
- an inner member;
- an outer member; and
- a suture connected to the inner member and the outer member, wherein a first portion of the suture is embedded within a second portion of the suture at an embedded portion such that as tension in the suture increases the first and second portions are held together,
- wherein the second portion completely encircles the first portion at at least one cross section, and
- wherein at least one of the inner member and the outer member are configured to seal an incision in a blood vessel,
- wherein the suture, the inner member and the outer member are arranged such that the inner member and the outer member lie opposite to one another with at least a portion of the suture in-between the inner member and the outer member, with the outer member being moveable along said portion towards the inner member,
- wherein the device to seal an incision in a blood vessel further comprises an introducer device, adapted to guide and push the inner member and the outer member in place during a sealing procedure, wherein the suture passes through the introducer device,
- wherein the suture has a first end at one bitter end of the suture and a second end at another bitter end of the suture and the suture is configured such that the first and second ends pass by each other in opposite directions such that the first end and the second end are on opposite sides of the embedded portion,
- wherein the suture forms a loop of fixed, unvariable length,
- wherein all ends of the suture are buried within the suture such that no suture ends are visible at any time,
- wherein the suture bitter ends are made of suture material.

17. A device to seal an incision in a blood vessel, comprising:
- an inner member;
- an outer member; and
- a suture connected to the inner member and the outer member, wherein a first portion of the suture is embedded within a second portion of the suture at an embedded portion such that as tension in the suture increases the first and second portions are held together,
- wherein the second portion completely encircles the first portion at at least one cross section, and
- wherein at least one of the inner member and the outer member are configured to seal an incision in a blood vessel,
- wherein the suture, the inner member and the outer member are arranged such that the inner member and the outer member lie opposite to one another with at least a portion of the suture in-between the inner member and the outer member, with the outer member being moveable along said portion towards the inner member,
- wherein all ends of the suture are buried within the suture such that no suture ends are visible at any time,
- wherein the device to seal an incision in a blood vessel further comprises an introducer device, adapted to guide and push the inner member and the outer member in place during a sealing procedure, wherein the suture passes through the introducer device,
- wherein the suture has a first end at one bitter end of the suture and a second end at another bitter end of the suture and the suture is configured such that the first and second ends pass by each other in opposite directions such that the first end and the second end are on opposite sides of the embedded portion,
- wherein the suture forms a loop of fixed, unvariable length,
- wherein the suture bitter ends are made of suture material.

18. A device to seal an incision in a blood vessel, comprising:
- an inner member;
- an outer member; and
- a suture connected to the inner member and the outer member, wherein a first portion of the suture is embedded within a second portion of the suture at an embedded portion such that as tension in the suture increases the first and second portions are held together,
- wherein the second portion completely encircles the first portion at at least one cross section, and
- wherein at least one of the inner member and the outer member are configured to seal an incision in a blood vessel,
- wherein the suture, the inner member and the outer member are arranged such that the inner member and the outer member lie opposite to one another with at least a portion of the suture in-between the inner member and the outer member, with the outer member being moveable along said portion towards the inner member,
- wherein the entire portion of the suture extending from the inner member to the outer member has no knots,
- wherein the device to seal an incision in a blood vessel further comprises an introducer device, adapted to guide and push the inner member and the outer member in place during a sealing procedure, wherein the suture passes through the introducer device,
- wherein the suture has a first end at one bitter end of the suture and a second end at another bitter end of the suture and the suture is configured such that the first and second ends approach each other from opposite directions,
- wherein the suture forms a loop of fixed, unvariable length,
- wherein all ends of the suture are buried within the suture such that no suture ends are visible at any time,
- wherein the suture bitter ends are made of suture material.

19. A device to seal an incision in a blood vessel, comprising:
- an inner member;
- an outer member; and
- a suture connected to the inner member and the outer member, wherein a first portion of the suture is embedded within a second portion of the suture at an embedded portion such that as tension in the suture increases the first and second portions are held together,
- wherein the second portion completely encircles the first portion at at least one cross section, and
- wherein at least one of the inner member and the outer member are configured to seal an incision in a blood vessel,
- wherein the suture, the inner member and the outer member are arranged such that the inner member and the outer member lie opposite to one another with at least a portion of the suture in-between the inner member and the outer member, with the outer member being moveable along said portion towards the inner member, wherein the entire portion of the suture extending from the inner member to the outer member has no knots, wherein the device to seal an incision in a blood vessel further comprises an introducer device, adapted to guide and push the inner member and the outer member in place during a sealing procedure, wherein the suture passes through the introducer device, wherein the suture has a first end at one bitter end of the suture and a second end at another bitter end of the suture and the suture is configured such that the first and second ends approach each other from opposite directions and then go beyond each other such that the first end and the second end are on opposite sides of the embedded portion, wherein the suture forms a loop of fixed, unvariable length, wherein all ends of the suture are buried within the suture such that no suture ends are visible at any time, wherein the suture bitter ends are made of suture material.

* * * * *